(12) United States Patent
Penzes et al.

(10) Patent No.: US 9,550,812 B2
(45) Date of Patent: Jan. 24, 2017

(54) SYNTHETIC CAPSID PROTEINS AND USES THEREOF

(75) Inventors: Zoltan Penzes, Budapest (HU); Anna Kollar, Budapest (HU); Marianna Ivok, Budapest (HU)

(73) Assignee: Ceva Sante Animale, Libourne (FR)

( * ) Notice: Subject to any disclaimer, the term of this patent is extended or adjusted under 35 U.S.C. 154(b) by 0 days.

(21) Appl. No.: 14/342,148

(22) PCT Filed: Aug. 31, 2012

(86) PCT No.: PCT/EP2012/066934
§ 371 (c)(1),
(2), (4) Date: Jul. 8, 2014

(87) PCT Pub. No.: WO2013/030320
PCT Pub. Date: Mar. 7, 2013

(65) Prior Publication Data
US 2014/0363459 A1 Dec. 11, 2014

(30) Foreign Application Priority Data
Sep. 2, 2011 (EP) .................................... 11306094

(51) Int. Cl.
*C07K 14/17* (2006.01)
*C07K 14/005* (2006.01)
*A61K 39/225* (2006.01)
*A61K 39/12* (2006.01)
*C07K 14/01* (2006.01)
*A61K 39/00* (2006.01)

(52) U.S. Cl.
CPC ............. *C07K 14/005* (2013.01); *A61K 39/12* (2013.01); *A61K 39/225* (2013.01); *C07K 14/01* (2013.01); *A61K 2039/5252* (2013.01); *A61K 2039/5256* (2013.01); *A61K 2039/552* (2013.01); *A61K 2039/55566* (2013.01); *C07K 14/17* (2013.01); *C12N 2710/14043* (2013.01); *C12N 2750/10022* (2013.01); *C12N 2750/10033* (2013.01); *C12N 2750/10034* (2013.01); *C12N 2750/10041* (2013.01)

(58) Field of Classification Search
CPC ........... C12N 2770/10034; C12N 2750/10043; C12N 2750/14143; C12N 2710/10322; C12N 2720/12334; C12N 2720/12352; A61K 2039/53; A61K 2039/525; A61K 39/00; C07K 14/005; C07K 16/10
See application file for complete search history.

(56) References Cited

U.S. PATENT DOCUMENTS

| | | | |
|---|---|---|---|
| 6,703,023 B1 * | 3/2004 | Jestin .................... | A61K 39/12 424/186.1 |
| 2009/0017064 A1 * | 1/2009 | Wu ....................... | A61K 39/12 424/205.1 |

FOREIGN PATENT DOCUMENTS

| | | |
|---|---|---|
| EP | 2275132 A2 | 1/2011 |
| WO | WO-99/29871 A2 | 6/1999 |
| WO | WO-2007/028823 A1 | 3/2007 |
| WO | WO-2010/061000 A1 | 6/2010 |

OTHER PUBLICATIONS

"Glycine max protein SEQ ID No. 238827.", XP002664422, retrieved from EBI accession No. GSP:AFQ47650, 2007.
Blanchard, et al., "Protection of swine against post-weaning multisystemic wasting syndrome (PMWS) by porcine circovirus type 2 (PCV2) proteins", Vaccine, Elsevier LTD, vol. 21, No. 31, 2003.
"Porcine circovirus 2 open reading frame 2 encoded protein, SEQ ID 2.", XP002664423, retrieved from EBI accession No. GSP:AYN62495, 2011.
Shang, et al., "Fine mapping of antigenic epitopes on capsid proteins of porcine circovirus, and antigenic phenotype of porcine circovirus Type 2", Molecular Immunology, Pergamon, vol. 46, No. 3, 2009.
Liu, et al., "Bacterial Expression of an Immunologically Reactive PCV2 ORF2 Fusion Protein", Protein Expression and Purification, Academic Press, vol. 21, No. 1, 2001.
Mahe, et al., "Differential recognition of ORF2 protein from type 1 and type 2 porcine circoviruses and identification of immunorelevant epitopes", Journal of General Virology, Society for General Microbiology, vol. 81, 2000.

* cited by examiner

*Primary Examiner* — Bao Li
(74) *Attorney, Agent, or Firm* — Cesari and McKenna LLP (57) ABSTRACT

The present invention relates to synthetic proteins and the uses thereof. More particularly, the invention relates to synthetic Circovirus type capsid proteins with improved properties. These proteins, or the coding nucleic acids, are useful e.g., to generate antibodies, immunogen compositions, or vaccines. The invention further relates to methods for treating and/or preventing PCV2-associated diseases in mammals using said proteins, nucleic acids or compositions. The invention also relates to compositions and methods for detecting PCV2 in a sample, using the above proteins, nucleic acids, or antibodies.

19 Claims, 1 Drawing Sheet

SYNTHETIC CAPSID PROTEINS AND USES THEREOF

CROSS-REFERENCE TO RELATED APPLICATIONS

This application is the National Stage of International Application No. PCT/EP2012/066934 filed on Aug. 31, 2012, which claims the benefit of European Patent Application No. 11306094.1 filed on Sep. 2, 2011. The contents of both applications are hereby incorporated by reference in their entirety.

FIELD OF THE INVENTION

The present invention relates to synthetic proteins and the uses thereof. More particularly, the invention relates to synthetic Circovirus type capsid proteins with improved properties. These proteins, or the coding nucleic acids, are useful e.g., to generate antibodies, immunogen compositions, or vaccines. The invention further relates to methods for treating and/or preventing PCV2-associated diseases in mammals using said proteins, nucleic acids or compositions. The invention also relates to compositions and methods for detecting PCV2 in a sample, using the above proteins, nucleic acids, or antibodies.

BACKGROUND OF THE INVENTION

Porcine circovirus (PCV) was originally identified as a contaminant of porcine kidney cell cultures (PK15 ATCC CCL-33). The PCV virion has been characterized as being an icosahedral, non-enveloped virus with a single-stranded circular DNA of about 1.76 kb. PCV was classified in the genus Circovirus of the Circoviridae family, which consists of other animal circoviruses such as psittacine beak-feather disease virus, goose circovirus, canary circovirus, and pigeon circovirus. Two genotypes of PCV have been recognized. The PK15 cell-derived PCV has been considered to be nonpathogenic to pigs, and is designated PCV type 1 (PCV1). On the other hand, PCV type 2 (PCV2) has been accepted as the major infectious agent involved in several pig diseases. PCV2 associated diseases cause significant economic losses to swine producers worldwide. PCV2 associated diseases are described in WO2007/076520 and include, for example, Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Occurrences of PCV2 subtype A (PCV2A) and PCV2 subtype B (PCV2B) have been reported particularly in 2000 in West Europe and in Central Europe in 2003. More recently similar changes have been reported in 2008 in wild boars.

Currently developed PCV2 vaccines, such as Circovac® (Merial), Ingelvac®, CircoFLEX (Boehringer Ingelheim Vetmedica), or Suvaxyn®, are either inactivated PCV2 vaccines or Sub-Unit vaccines. Regarding inactivated PCV2 vaccines, current PCV2 strains subtype A or B present several weaknesses. Particularly, PCV2 viruses can only be produced at low titers, generally less than 10<5> TCID50 viral particles per ml. Also, these viruses cannot be maintained in tissue cultures and permanently infected cell lines. Regarding PCV2A Sub-Unit vaccines, they typically use a purified, recombinant PCV2A capsid protein produced by expression of the ORF2 gene of PCV2A in a baculovirus system. In this regard, the protein encoded by ORF2 of PCV2 isolates Imp1011 has been reported in EP1741785. A protein encoded by ORF2 of PCV2 isolate PCV2Rm has been reported in WO2010/061000. The protein encoded by ORF2 of PCV2 isolate 412 has been reported in EP1816200. Another protein encoded by an ORF2 of a further PCV2 isolate has been reported in EP1036180 or EP2225367.

Expression efficiency and immunogenicity of these natural capsid proteins are, however, not optimal and do not always provide the required level of immune protection in vaccinated animals.

Accordingly, there is a need for alternative vaccine compositions to improve the efficacy of treatment or prevention of PCV2 infections in mammals, particularly in pigs.

SUMMARY OF THE INVENTION

The present invention discloses synthetic capsid proteins with improved properties. These proteins may be used either alone or in combination with other capsid protein or immunogens, to produce an improved protective or defensive immunity against PCV2 infection in mammals.

An object of the invention therefore relates to proteins comprising a sequence selected from SEQ ID NO: 2, 4 or 6, or a sequence having at least 85% identity to any one of said sequences.

A further object of the invention relates to a fragment of a protein as defined above, said fragment comprising at least 8, 10, 12, 15, or 20 consecutive amino acids of said protein.

A further object of the invention relates to a protein or peptide comprising SEQ ID NO: 7 or a fragment of SEQ ID NO: 7 comprising at least 8 consecutive amino acid residues.

A further object of the invention resides in an antigen comprising a protein or fragment as defined above.

A further object of the invention is a chimeric polypeptide comprising a protein or peptide as defined above and a carrier amino acid sequence linked to or inserted into said protein or peptide. The carrier amino acid sequence may be any sequence that facilitates e.g., expression, purification, or immunogenicity of the protein or peptide.

The invention also relates to a nucleic acid molecule encoding a protein, peptide or polypeptide as defined above. The invention also relates to a vector comprising such a nucleic acid molecule, typically under the control of a promoter.

A further object of the invention resides in a binding reagent that specifically binds a protein or nucleic acid molecule as defined above. Such a binding reagent is preferably selected from an antibody (or a fragment or derivative of an antibody), or a nucleic acid primer or probe.

Another object of the present invention is a composition comprising a protein, peptide, polypeptide, nucleic acid or vector as defined above. The composition may further comprise an excipient and/or an adjuvant. The composition may be used as an immunogen, to produce specific antibodies. The composition may be a vaccine.

In this regard, a particular object of the invention is a vaccine composition comprising an immunologically effective amount of a protein, peptide, polypeptide, nucleic acid, or vector as defined above and, optionally, an excipient and/or an adjuvant. The vaccine may comprise additional active ingredients such as one or several additional protein antigens.

The invention also relates to a method of producing such a vaccine, as well as to the use of such a vaccine for treating mammals.

A further aspect of the invention relates to methods of treating and/or preventing PCV2 associated diseases in a non-human mammal, and to methods of immunizing or vaccinating a non human animal subject, such as pigs, swine, piglet, against PCV2 infections, comprising administering to said animal subject a protein, nucleic acid or vaccine composition as defined above.

The invention also relates to a protein or antigen as defined above for use to treat or prevent PCV2 associated diseases in a non-human mammal.

According to another aspect, the present invention provides a method of diagnosing the presence of PCV2 virus in a sample, reagents used therefor, as well as diagnostic kits and diagnostic tests.

The invention also relates to a recombinant cell comprising a nucleic acid as defined above encoding a protein of the invention.

The invention further relates to a method for producing a protein of the invention comprising culturing a cell as defined above under conditions allowing expression of the nucleic acid and recovering the protein.

DETAILED DESCRIPTION OF THE INVENTION

The present invention relates inter alia to synthetic proteins, nucleic acids, as well as vaccine compositions suitable to prevent PCV2-associated diseases in non-human animals.

Synthetic Capsid Protein

An object of the invention relates to synthetic capsid proteins with improved properties. These proteins are useful e.g., to generate antibodies, immunogen compositions, or vaccines.

The proteins of the invention have been designed by the inventors to provide improved immunogenic and expression properties. They are distinct from naturally-occurring capsid proteins of porcine circovirus. These proteins exhibit a specific and potent immunogenic capacity, allowing the generation of a protective immunity in animals. These proteins can be efficiently expressed in recombinant host cells. These proteins, or fragments thereof, therefore represent novel active agents which can be used to produce efficient vaccine compositions.

An object of the invention therefore relates to a protein comprising a sequence selected from SEQ ID NO: 2, 4 or 6, or a sequence having at least 85% identity to any one of said sequences. Preferred proteins exhibit at least 90% amino acid sequence identity to SEQ ID NO: 2, 4 or 6, even more preferably at least 95%, 96%, 97% or 98%. The extent of sequence identity may be determined using any computer program and associated parameters, including BLAST 2.2.2 or FASTA version 3.0t78, with the default parameters.

In a particular embodiment, the protein comprises the sequence of SEQ ID NO: 2 or a sequence having at least 85% identity thereto, even more preferably at least 90% amino acid sequence identity, further more preferably at least 95%.

A further object of the invention relates to a protein or peptide comprising at least SEQ ID NO: 7, or any fragment of at least 8 consecutive amino acids residues of SEQ ID NO: 7.
SFTKKKFKK K(NorH)K(TorP)KTHV(SorG)Q V(VorL) KKKT(RorW)VL(QorH) TK(YorH)KFKWKKR SEQ ID NO: 7 essentially corresponds to amino acids 3-42 of SEQ ID NO: 2. This sequence contains epitopes which contribute to the immunogenic activity of the proteins of the invention. In SEQ ID NO: 7, amino acid at position 12 is N or H, amino acid at position 14 is T or P, amino acid at position 19 is S or G, amino acid at position 22 is V or L, amino acid at position 27 is R or W, amino acid at position 30 is Q or H, and amino acid at position 33 is Y or H.

A particular object of the invention relates to a protein or peptide comprising at least amino acids 1-11 of SEQ ID NO: 7.

A further particular object of the invention relates to a protein or peptide comprising at least amino acids 12-26 of SEQ ID NO: 7.

A further particular object of the invention relates to a protein or peptide comprising at least amino acids 25-35 of SEQ ID NO: 7.

As indicated above, another object of the invention resides in a fragment of a protein as defined above. A particular example of such a fragment is the mature form of the protein, which is devoid of a leader peptide sequence and/or of a pre-sequence. A particular and preferred example of such a protein comprises amino acid residues 43 to 234 of SEQ ID NO: 2.

A further object of the invention resides in a protein antigen comprising a peptide as defined above.

Preferred proteins of the invention contain less than 300 amino acids. Most preferred proteins of the invention are immunogenic in a mammal and can induce or stimulate an immune response against a PCV2 virus.

The proteins of the invention may be further modified to improve e.g., their stability or activity. In this regard, in a particular embodiment, the proteins or peptides of the invention contain a carrier amino acid sequence, which may be fused to an end of the protein or inserted within the protein sequence. The term "fused" or "inserted" typically indicates that the two moieties are linked through a peptide link. However, any other link may be contemplated, e.g., chemical. Furthermore, two moieties may be fused either directly or through a spacer sequence, to facilitate e.g., cloning and/or subsequent cleavage. The carrier may be fused to the N-terminal end of the protein or peptide, or to the C-terminal end thereof. The carrier amino acid sequence may be synthetic, natural or artificial, and used to confer on the fusion polypeptide improved expression, purification or immunogenic properties. The carrier sequence may contain e.g., from 3 to 500 amino acids. The carrier amino acid sequence is preferably immunologically inert and/or does not alter the immunoreactivity of the protein or peptide. In a particular embodiment, the carrier is a protein, particularly a mammalian protein, such as serum albumin (e.g., human, bovine, pig). In this regard, a particular object of the invention resides in a fusion polypeptide comprising a protein or peptide of the invention fused at its N- or C-terminal end to an albumin or an albumin domain. The invention shows surprisingly that these constructs are expressed at higher yields in yeasts cells. In this regard, an object of the invention resides in a fusion protein comprising (i) the amino acid sequence of a PCV2 antigen fused to (ii) the amino acid sequence of an albumin or an albumin domain. As a specific example, the amino acid sequences of a pig albumin or pig albumin domain 1 are provided as SEQ ID NOs: 8 and 9, respectively. These amino acid sequences are preferably fused to the N-terminal amino acid of a PCV2 protein antigen.

In another embodiment, the carrier amino acid sequence is a tag (or flag) sequence, which may be inserted in the protein. An example of a tag is, for instance, the sequence DYKDDDDK (SEQ ID NO: 10). Such a sequence can be inserted e.g., between amino acids 1 and 2 of a protein of SEQ ID NO: 2, 4, or 6, to facilitate purification or identification.

The proteins or peptides or polypeptides of the invention may be produced by recombinant techniques, or they may be artificially produced. They may be in soluble form, or on solid phase. In particular, they may be bound to cell membranes or lipid vesicles, or to synthetic supports such as glass, plastic, polymers, filter, membranes, e.g., in the form of beads, columns, plates and the like.

The proteins, peptides or polypeptides of the invention are typically provided in an isolated form. The term "isolated" is meant to refer to a protein which is in other than a native environment. For example, the protein may be a component of a cell culture or other artificial medium; a component of a pharmaceutical composition; or partially or completely purified from its native environment.

In a particular embodiment, a composition is used which comprises the protein as a partially purified cell supernatant. The cell supernatant may contain cell proteins, DNA fragments, and the like. The supernatant is preferably enriched for the protein of the invention and, even more preferably, treated to inactivate or destroy any nucleic acid or virus present in the composition.

The proteins and peptides of the invention may be purified by techniques known per se in the art, and stored under conventional techniques. They may be used as such, in purified form, either alone or in combinations.

Nucleic Acid Molecules and Recombinant Host Cells

The invention also relates to a nucleic acid molecule encoding a protein or peptide as defined above. The invention also relates to a vector comprising such a nucleic acid molecule, typically under the control of a promoter.

The invention also relates to a recombinant cell comprising a nucleic acid as defined above.

The invention further relates to a method for producing a protein of the invention comprising culturing a cell as defined above under conditions allowing expression of the nucleic acid and recovering the protein.

Nucleic acid molecules of the invention may be DNA or RNA, double-stranded or single-stranded, analogues of DNA and RNA, such as those containing modified backbones. Single-stranded DNA or RNA may be the coding strand, also known as the sense strand, or it may be the non-coding strand, also referred to as the anti-sense strand.

The nucleic acid molecules of the invention typically comprise:
  a) a nucleotide sequence selected from SEQ ID NOs: 1, 3, or 5, or a nucleotide sequence having an homology of at least 85%, 90%, 95%, 96%, 97%, 98%, or 99%, with any one of the nucleotide sequence of SEQ ID NO: 1, 3 or 5, or
  b) a nucleotide sequence which is capable of hybridizing to a nucleotide sequence of SEQ ID NO: 1, 3 or 5, under conditions of high stringency, or
  c) a sequence corresponding to a sequence of a) or b) within the degeneration of the genetic code.

The degree of homology between two nucleic acid sequences may be determined by means of computer programs known in the art such as GAP provided in the GCG program package (Program Manual for the Wisconsin Package, Version 8, August 1996, Genetics Computer Group, 575 Science Drive, Madison, Wis., USA 5371 1) (Needleman, S. B. and Wunsch, C D., (1970), Journal of Molecular Biology, 48, 443-453). Using GAP with the following settings for DNA sequence comparison: GAP creation penalty of 5. 0 and GAP extension penalty of 0.3. Nucleic acid molecules may be aligned to each other using the Pileup alignment software, available as part of the GCG program package, using, for instance, the default settings of gap creation penalty of 5 and gap width penalty of 0.3.

Suitable experimental conditions for determining whether a given nucleic acid molecule hybridises to a specified nucleic acid may involve pre-soaking of a filter containing a relevant sample of the nucleic acid to be examined in 5×SSC for 10 minutes, and pre-hybridisation of the filter in a solution of 5×SSC, 5×Denhardt's solution, 0.5% SDS and 100 [mu]g/ml of denatured sonicated salmon sperm DNA, followed by hybridisation in the same solution containing a concentration of 10 ng/ml of a P-dCTP-labeled probe for 12 hours at approximately 45<0>C, in accordance with the hybridisation methods as described in Sambrook et al. (1989; Molecular Cloning, A Laboratory Manual, 2nd edition, Cold Spring Harbour, N.Y.). The filter is then washed twice for 30 minutes in 2×SSC, 0.5% SDS at least 55 <0>C (low stringency), at least 60<0>C (medium stringency), at least 65<0>C (medium/high stringency), at least 70<0>C (high stringency), or at least 75<0>C (very high stringency). Hybridisation may be detected by exposure of the filter to an x-ray film.

The nucleic acid molecules according to the invention may be provided in the form of a nucleic acid molecule per se such as naked nucleic acid molecules; a vector; virus or host cell etc, either from prokaryotic or eukaryotic origin. Vectors include expression vectors that contain a nucleic acid molecule of the invention. The vectors of the present invention may, for example, comprise a transcription promoter, and a transcription terminator, wherein the promoter is operably linked with the nucleic acid molecule, and wherein the nucleic acid molecule is operably linked with the transcription terminator.

In this regard, a particular object of the invention is a baculovirus vector comprising a nucleic acid as defined above.

The use of a baculovirus expression system is advantageous as it provides high yields of high antigenic material suitable for vaccination. In addition, there is no need to purify the protein as the baculovirus (preferably inactivated) may be used directly in the vaccine. In the baculovirus vector, the nucleic acid of the invention should be inserted under the control of a promoter, preferably a baculovirus endogenous promoter, such as the polyhedrin or p10 gene promoter.

After the protein is produced inside the recombinant baculovirus infected cells, the cells are typically disrupted by physical means (e.g., ultrasound, freeze-thaw, or high pressure homogenization) to release the produced protein from the cells. The crude insect cell lysate is then removed by centrifugation, and the supernatant may be used as the antigen for the vaccine. The disrupted insect cell lysate may contain recombinant live baculovirus in high titer. Even if the recombinant baculovirus is not able to live/replicate in a formulated vaccine or if it is injected into pigs, the baculovirus is preferably inactivated or killed prior to use of the antigen, using techniques known per se in the art.

Other expression systems and vectors may be used as well, such as plasmids that replicate and/or integrate in yeast cells.

A particular embodiment of the invention is a vector comprising a nucleic acid of the invention and a further nucleic acid molecule encoding a distinct viral or pathogenic antigen. Such a vector may be used as a multivalent vaccine, or to produce a multivalent vaccine. Specific examples of distinct viral or pathogenic antigens include any protein (e.g., glycoprotein, capsid protein, or antigen-fragment thereof) of a virus or pathogen selected from e.g., *Actinobacillus pleuropneunomia; Adenovirus; Alphavirus* such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* sp. and preferably *C. pecorum and C. abortus; Clostridium* spp., preferably *Cl. difficile, Cl. perfringens* types A, B and C, *Cl. novyi, Cl. septicum, Cl. tetani*; Digestive and respiratory Coronavirus; *Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; *Isospora suis; Japanese Encephalitis* virus; *Lawsonia intracellulars; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellular* and *M. bovis: Mycoplasma hyponeumoniae; Parvovirus; Pasteurella multocida; Porcine cytomegolovirus; Porcine parovirus, Porcine reproductive* and respiratory syndrome virus: *Pseudorabies virus; Rotavirus; Sagiyama virus; Salmonella* spp. preferably, *S. thyhimurium* and *S. choleraesuis; Staphylococcus* spp. preferably, *S. hyicus; Streptococcus* spp., preferably *Strep, suis; Swine cytomegalovirus; Swine herpes* virus; *Swine influenza* virus; *Swine pox* virus; *Toxoplasma gondii; Vesicular stomatitis* virus and virus of exanthema of swine; or other isolates and subtypes of porcine circo virus. In such a vector, the at least two coding nucleic acids may be under the control of the same or distinct promoter. They may be in the same or opposite orientation.

In a further embodiment of the invention, there is provided a host cell transformed with a nucleic acid molecule or vector according to the invention. Suitable examples of host cells will be known to those skilled in the art or can be readily selected by those skilled in the art. Host cells may, for example, include eukaryotic and prokaryotic cells. Examples of eukaryotic cells include mammalian (e.g., pig), fungal (e.g. *Saccharomyces cerevisiae, pichia, aspergillus, fusarium*), insect and plant cells. Prokaryotic cells include, for example, *E. coli*. Preferred host cells of the invention are insect cells (in such a case the vector is preferably a baculovirus vector) or yeast cells.

The invention also relates to a method for preparing a protein, peptide or polypeptide of the invention, the method comprising culturing a host cell containing a nucleic acid or vector as defined above under conditions suitable for expression of the nucleic acid and recovering the protein, peptide, or polypeptide. As indicated above, the proteins and peptides may be purified according to techniques known per se in the art. The invention also provides expression kits comprising (a) a host cell (preferably insect cells or yeast cells), (b) means of expressing a protein or peptide or polypeptide of the invention, e.g. comprising a vector system capable of being replicated in said cell, and (c) means of recovering the protein or peptide of the invention.

Vaccine Compositions

The term "vaccine" as used herein includes an agent which may be used to cause, stimulate or amplify the immune system of animals (e.g., pigs) against a pathogen. Vaccines of the invention are able to cause or stimulate or amplify immunity against a PCV2 virus.

The term "immunization" includes the process of delivering an immunogen to a subject. Immunization may, for example, enable a continuing high level of antibody and/or cellular response in which T-lymphocytes can kill or suppress the pathogen in the immunized non human animal, such as pig, which is directed against a pathogen or antigen to which the animal has been previously exposed.

Vaccines of the invention comprise an immunologically effective amount of a protein or peptide as described above in a pharmaceutically acceptable vehicle. As a result of the vaccination with a composition of the invention, animals become at least partially or completely immune to PCV2 infections, or resistant to developing moderate or severe PCV2 infections. PCV2 vaccines may be used to elicit a humoral and/or a cellular response.

PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors. Preferably, a non human animal subject, such as pig, is protected to an extent in which one to all of the adverse physiological symptoms or effects of PCV2 infections are significantly reduced, ameliorated or totally prevented.

The present invention also relates to a combination vaccine comprising a protein of the invention in combination with at least one additional PCV2 protein antigen [Gupi P. S. Nayar et al. (Can. Vet. J, vol. 38, 1997: 385-387) and Clark E. G. (Proc. Am. Assoc. Swine Prac. 1997; 499-501)].

In practice, the exact amount required for an immunologically effective dose may vary from subject to subject depending on factors such as the age and general condition of the subject, the nature of the formulation and the mode of administration. Appropriate "effective amount" may be determined by one of ordinary skill in the art using only routine experimentation. For instance, methods are known in the art for determining or titrating suitable dosages of a vaccine to find minimal effective dosages based on the weight of the non human animal subject, concentration of the vaccine and other typical factors.

In a typical embodiment, the vaccine comprises a unitary dose of between 0.1-50 µg, preferably between 0.1 and 25, even more preferably of between 1 and 15 µg, typically approx. 10 µg, of protein or peptide antigen of the invention.

The dosage of the vaccine, concentration of components therein and timing of administering the vaccine, which elicit a suitable immune response, can be determined by methods such as by antibody titrations of sera, e.g., by ELISA and/or seroneutralization assay analysis and/or by vaccination challenge evaluation.

In a particular embodiment, the vaccine comprises the protein or peptide antigen of the invention in purified form.

In another particular embodiment, the protein or peptide antigen is linked to a carrier material. In this regard, in a specific embodiment, the protein or peptide is displayed by a baculovirus.

Vaccines may comprise other ingredients, known per se by one of ordinary skill in the art, such as pharmaceutically acceptable carriers, excipients, diluents, adjuvants, freeze drying stabilizers, wetting or emulsifying agents, pH buffering agents, gelling or viscosity enhancing additives, and preservatives, depending on the route of administration.

Examples of pharmaceutically acceptable carriers, excipients or diluents include, but are not limited to demineralised or distilled water; saline solution; vegetable based oils such as peanut oil, arachis oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methyl cellulose, ethyl cellulose, carboxymethylcellulose, carboxymethylcellulose sodium salt, or hydroxypropyl methylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia, and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-[alpha], IFN-[beta], IFN-y, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

Examples of freeze-drying stabilizer may be for example carbohydrates such as sorbitol, mannitol, starch, sucrose, dextran or glucose, proteins such as albumin or casein, and derivatives thereof.

Vaccines may additionally comprise at least one immunogen from at least one additional pathogen, eg., a pig pathogen such as *Actinobacillus pleuropneunomia; Adenovirus; Alphavirus* such as Eastern equine encephalomyelitis viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani*; Digestive and respiratory *Coronavirus; Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; lsospora suis; *Japanese Encephalitis* virus; *Lawsonia intracellulars; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellular* and *M. bovis: Mycoplasma hyponeumoniae; Parvovirus; Pasteurella multocida; Porcine cytomegolovirus; Porcine parovirus, Porcine reproductive* and respiratory syndrome virus: *Pseudorabies virus; Rotavirus; Sagiyama virus; Salmonella* spp. preferably, *S. thyhimurium* and *S. choleraesuis; Staphylococcus* spp. preferably, *S. hyicus; Streptococcus* spp., preferably Strep, suis; Swine cytomegalovirus; Swine herpes virus; Swine influenza virus; Swine pox virus; *Toxoplasma gondii; Vesicular stomatitis* virus and virus of exanthema of swine; or other isolates and subtypes of porcine circo virus.

The vaccine compositions of the invention may be liquid formulations such as an aqueous solution, water-in-oil or oil-in-water emulsion, syrup, an elixir, a tincture, a preparation for parenteral, subcutaneous, intradermal, intramuscular or intravenous administration (e.g., injectable administration), such as sterile suspensions or emulsions. Such formulations are known in the art and are typically prepared by dissolution of the antigen and other typical additives in the appropriate carrier or solvent systems. Liquid formulations also may include suspensions and emulsions that contain suspending or emulsifying agents.

The route of administration can be percutaneous, via mucosal administration, or via a parenteral route (intradermal, intramuscular, subcutaneous, intravenous, or intraperitoneal). Vaccines compositions according to the present invention may be administered alone, or can be co-administered or sequentially administered with other treatments or therapies. Vaccines of the invention may, in addition, comprise one or several additional protein antigens from different PCV2 serotypes.

The present invention also relates to methods of immunizing or inducing an immune response in non-human mammals (e.g., pigs) comprising administering to said mammal a protein, peptide, nucleic acid or vaccine as described above.

The present invention also relates to methods of treating and/or preventing PCV2 associated diseases in non-human mammals (e.g., pigs) comprising administering to said mammal a protein, peptide, nucleic acid or vaccine as described above.

As mentioned above, PCV2 infections or associated diseases include inter alia Postweaning Multisystemic Wasting Syndrome (PMWS), Porcine Dermatitis and Nephropathy Syndrome (PDNS), Porcine Respiratory Disease Complex (PRDC), reproductive disorders, granulomatous enteris, exsudative epidermitis, necrotizing lymphadenitis, and congenital tremors.

The vaccine of the invention can conveniently be administered intranasally, transdermally (i.e., applied on or at the skin surface for systemic absorption), parenterally, ocularly, etc. The parenteral route of administration includes, but is not limited to, intramuscular, intravenous, intraperitoneal routes and the like.

The dosage of the vaccines of the present invention will depend on the species, breed, age, size, vaccination history, health status of the animal to be vaccinated, as well as of the route of administration, e.g., subcutaneous, intradermal, oral intramuscular or intravenous administration.

The vaccines of the invention can be administered as single doses or in repeated doses. The vaccines of the invention can be administered alone, or can be administered simultaneously or sequentially administered with one or more further compositions, such as for example other porcine immunogenic or vaccine compositions. Where the compositions are administered at different times the administrations may be separate from one another or overlapping in time.

In one embodiment, the vaccine compositions of the invention are administered to a subject susceptible to or otherwise at risk for PCV2 infection to enhance the subject own immune response capabilities. The subject to which the vaccine is administered is in one embodiment a pig. The animal may be susceptible to infection by PCV2 or a closely related virus.

Vaccines of the invention are preferably administered to pigs, adult pigs, but also to young pigs, piglets or to pregnant females, or to other types of non human mammals. Vaccination of pregnant females is particularly advantageous as it confers passive immunity to the newborns via the transmission of maternal antibodies. The pigs may be less than 7, 6, 5, 4, 3, 2 or 1 week old; 1 to 6 weeks old; 2 to 5 weeks old; or 3 to 4 weeks old. For instance, "test" animals may be administered the vaccine of the invention in order to evaluate the performance of the vaccine with a view to eventual use or development of a vaccine for pigs. Desirably, the vaccine is administered to a subject who has not yet been exposed to a PCV2 virus. Preferably, the subject is a pig which is in need of vaccination against Postweaning Multisystemic Wasting Syndrome (PMWS) and/or Porcine Dermatitis and Nephropathy Syndrome (PDNS).

The present invention also includes a combination vaccine, comprising vaccines of the invention and at least one immunogenic active component effective against another disease-causing organism in swine such as for example *Actinobacillus pleuropneunomia; Adenovirus; Alphavirus* such as *Eastern equine encephalomyelitis* viruses; *Balantidium coli; Bordetella bronchiseptica; Brachyspira* spp., preferably *B. hyodyentheriae, B. pilosicoli, B. innocens, Brucella suis*, preferably biovars 1, 2 and 3; Classical swine fever virus, African swine fever virus; *Chlamydia* and *Chlamydophila* sp. and preferably *C. pecorum* and *C. abortus; Clostridium* spp., preferably *Cl. difficile, Cl. perfringens* types A, B and C, *Cl. novyi, Cl. septicum, Cl. tetani;* Digestive and respiratory *Coronavirus; Cryptosporidium parvum; Eimeria* spp; *Eperythrozoonis suis* currently named *Mycoplasma haemosuis; Erysipelothrix rhusiopathiae; Escherichia coli; Haemophilus parasuis*, preferably subtypes 1, 7 and 14; Hemagglutinating encephalomyelitis virus; Isospora suis; *Japanese Encephalitis* virus; *Lawsonia intracellulars; Leptospira* spp., preferably *Leptospira australis, Leptospira canicola, Leptospira grippotyphosa, Leptospira icterohaemorrhagicae, Leptospira interrogans, Leptospira Pomona* and *Leptospira tarassovi; Mannheimia haemolytica; Mycobacterium* spp. preferably, *M. avium, M. intracellular* and *M. bovis: Mycoplasma hyponeumoniae; Parvovirus; Pasteurella multocida; Porcine cytomegolovirus; Porcine parovirus*, Porcine reproductive and respiratory syndrome virus: *Pseudorabies virus; Rotavirus; Sagiyama* virus; *Salmonella* spp. preferably, *S. thyhimurium* and *S. choleraesuis; Staphylococcus* spp. preferably, *S. hyicus; Streptococcus* spp., preferably Strep, suis; *Swine cytomegalovirus; Swine herpes* virus; *Swine influenza* virus; *Swine pox* virus; *Toxoplasma gondii; Vesicular stomatitis* virus and virus of exanthema of swine or other isolates and subtypes of porcine circo virus.

The present invention also provides a container comprising an immunologically effective amount a protein, nucleic acid or vaccine as described above. The invention also provides vaccination kits comprising an optionally sterile container comprising an immunologically effective amount of the vaccine, means for administering the vaccine to animals, and optionally an instruction manual including information for the administration of the immunologically effective amount the composition for treating and/or preventing PCV2 associated diseases.

Diagnostic Compositions and Methods

A further object of the invention resides in a method of diagnosing the presence of a circovirus in non-human animals, reagents used therefor, and diagnostic kits.

Based on the nucleotide sequences as described above, it is possible to produce reagents capable of recognizing porcine circoviruses. A skilled person in the art would be able to select fragments of around 20 to 50 bp within SEQ ID NO: 1, 3, or 5, in order to carry a specific diagnosis. Therefore, DNA sequences disclosed herein and their fragments may be used as probes and/or primers for detecting presence of circovirus by hybridization or PCR experiments. Antigens encoded by the virus or expressed via a vector may also be used as a reagent for diagnostic purpose may be detected by immunofluorescence or Western blotting experiments. Monoclonal or polyclonal antibodies as described above may be used in diagnostic tests and reagents according to techniques which are well known in the art, for example by ELISA and immunochromatography.

The present invention further relates to a method of generating an antibody which is capable of binding to a PCV2 virus. The method may comprise immunizing a non-human animal, such as a rabbit, guinea pig, or rodent, with a protein or peptide of the invention and harvesting the antibody produced thereby. The antibodies of the invention may be polyclonal or monoclonal antibody preparations, monospecific antisera, human antibodies, or may be hybrid or chimeric antibodies, such as humanized antibodies, altered antibodies (Fab')2 fragments, F(ab) fragments, Fc fragments, single-domain antibodies, dimeric or trimeric antibody fragments or constructs, or functional fragments thereof which bind to the antigen in question. Antibodies may be produced using techniques well known per se to those of skill in the art and disclosed in "A Laboratory Manual, Harlow and Lane, eds., Cold Spring Harbor Laboratory, N.Y. (1988)".

Diagnostic kit thus may comprise DNA probes or primers, antigens and/or polyclonal or monoclonal antibodies specific for the proteins of the invention, and diagnostic testing may be performed on a sample of physiological fluid (blood, plasma, serum and the like) or a sample of tissue (ganglia, liver, lungs, kidneys and the like) obtained from a pig to be tested.

The invention further relates to an antibody (or a derivative or fragment thereof) that specifically binds a protein or peptide of the invention.

The invention also relates to an antibody (or a derivative or fragment thereof) that binds an epitope contained in SEQ ID NO: 7.

Further aspects and advantages of the invention are provided in the following section, which should be considered as illustrative only.

EXAMPLES

A. Synthesis and Structure of PRO1 and PRO2

PRO1 (SEQ ID NO: 2) and PRO2 (SEQ ID NO: 4) were designed by the inventors to provide improved vaccines against PCV2 infection. Starting from an analysis of multiple naturally occurring viral capsid proteins, the inventors have designed and conceived new and artificial proteins. These proteins are structurally distinct from naturally-occurring capsid proteins and exhibit potent immunogenicity. They can efficiently be produced from recombinant host cells.

Two proteins were produced. Their sequence is set forth in SEQ ID NO: 2 and 4. The sequence of a coding nucleic acid is represented in SEQ ID NO: 1 and 3, respectively. The nucleotide sequences of these proteins were constructed and cloned into an expression vector. The expression vector was used to (i) replicate and maintain the nucleic acid in a bacterial host and (ii) to produce the protein.

B. Synthesis and Structure of PRO3 (SEQ ID NO: 6)

PRO2 (SEQ ID NO: 4) sequence was used a reference sequence and modified further to create PRO3 sequence: Among others, the following optimizations were performed:
A potential cleavage site was eliminated at amino acid position 165.
A mutation was introduced in position 200.
A replacement was made in position 161.
A replacement was made in position 170.
The S residue in position 225 was replaced with a D.
replacement was made at position 143.
Two replacements were made at the N-terminal of the sequence (positions 13 and 20).

The nucleotide sequence was constructed and cloned into an expression vector. The sequence is represented in SEQ ID NO: 5. The encoded protein sequence is represented as SEQ ID NO: 6. The expression vector is used to (i) replicate and maintain the nucleic acid in a bacterial host and (ii) to produce the protein.

C. Expression of PRO1 and Immunogenicity

PRO1 was expressed successfully in Sf9 cells resulting in a product which had the expected antigenic properties. Western blot showed that the protein has the expected molecular weight and PRO1 protein was detected by different PCV2 mAbs in ELISA experiments.

C1: Generation of Recombinant Baculoviruses

The linearized baculovirus DNA (BD BaculoGold™ viral DNA, Cat. No. 554739), recombinant baculovirus transfer vector DNA containing the insert gene (pVL1393-Flag-PRO1) and PolyFect Transfection Reagent (Qiagen Cat. No. 301105) were mixed in Insect-Xpress Protein-Free medium (Lonza, Cat. No. 12-730Q) and incubated with freshly seeded Sf9 insect cells (Invitrogen #12659-017) at 27° C. for 6 days.

C2: Virus Amplification

Sf9 cells in log phase were used in 175 cm² tissue culture flask (at 50-70% confluency, approximately $2.5\text{-}3.5 \times 10^7$ cells/flask). One ml of the virus stock (see Example 1) and 4 ml of fresh Lonza serum free medium supplemented with Penicillin-Streptomycin Solution (Sigma Cat. No.: P4333) were mixed and added to the cells. The cells were incubated at 27° C. for 3 hours then 15 ml fresh medium was added to the infected cells, and the cells were incubated at 27° C. for further 5-6 days. Since the virus particles were released into the medium, the supernatant was harvested by pipetting the medium into a sterile 50 ml polypropylene tube. The suspension was centrifuged at 2000 g for 5 minutes and the stock was stored at 4° C. Virus amplification was done several times to achieve high virus titer. For the first amplification the supernatant of the co-transfection was used, later the generated virus stocks. Passage 3 virus stock was used for protein production.

C3: Recombinant Protein Expression in Sf9 Cells

Sf9 cells in log phase were used in 175 cm² tissue culture flasks (confluency 70-80%). Half ml of the high titer viral stock and fresh medium supplemented with penicillin-streptomycin were added to the cells. The cells were incubated at 27° C. for 3 hours, then 15 ml fresh medium was added to the transfected cells. The cells were incubated further at 27° C. for 4-5 days. The cells were removed from the flask with a cell scraper (Sarstedt 83.1830) and were centrifuged at 2500 g for 5 minutes. After discarding the supernatant the cell cultures were resuspended in 1 ml PBS buffer (GIBCO, Cat. No.: 14040). The resuspended cells were collected, the suspension was sonicated four times for 40 seconds. The sonicated suspension was centrifuged at 3000 g for 10 minutes at 4° C. The supernatant was transferred into a fresh tube and centrifuged at 5000 g for 10 minutes at 4° C. The supernatant was transferred into a fresh tube and stored at −20° C.

C4: Detection of Baculo-PRO1 Antigen by Immune-Fluorescence

Sf9 cells in 24-well plates ($4 \times 10^6$/well) were infected with 10-fold dilutions of Baculo PRO1 virus. The plates were incubated for 4 days at 27° C. After incubation plates were fixed with pre-chilled acetone for 30 minutes at 4° C. After fixation, plates were washed three times in phosphate buffered saline solution (PBS). After washing, primary antigen (VMRD, Cat. No.: PAB-PCV2, 1:500 dilution) was layered on the wells and incubated for 30 minutes at 37° C., then washed three times in PBS. Finally, secondary conjugate (anti-pig IgG-FITC antibody produced in rabbit, SIGMA, Cat. No.: F-1638, 1:1000 dilution) was layered on the fixed tissue culture for 30 minutes at 37° C., then plates were washed three times in PBS. The presence of Baculo PRO1 was detected by UV microscope.

C5: Inactivation of Baculo PRO1 and Formulation

The harvested BaculoPRO1 sample was inactivated with 300 μg/ml ethylene imine at 37° C. for 24 hours. The control of inactivation was performed on Sf9 cell line. The inactivated baculovirus is unable to infect Sf9 cells.

In the following examples, the vaccine composition used comprises the inactivated baculoPRO1 formulated in a water-in-oil emulsion.

C6: Detection of Baculo PRO1 Protein by Western Blot

Figure 1:
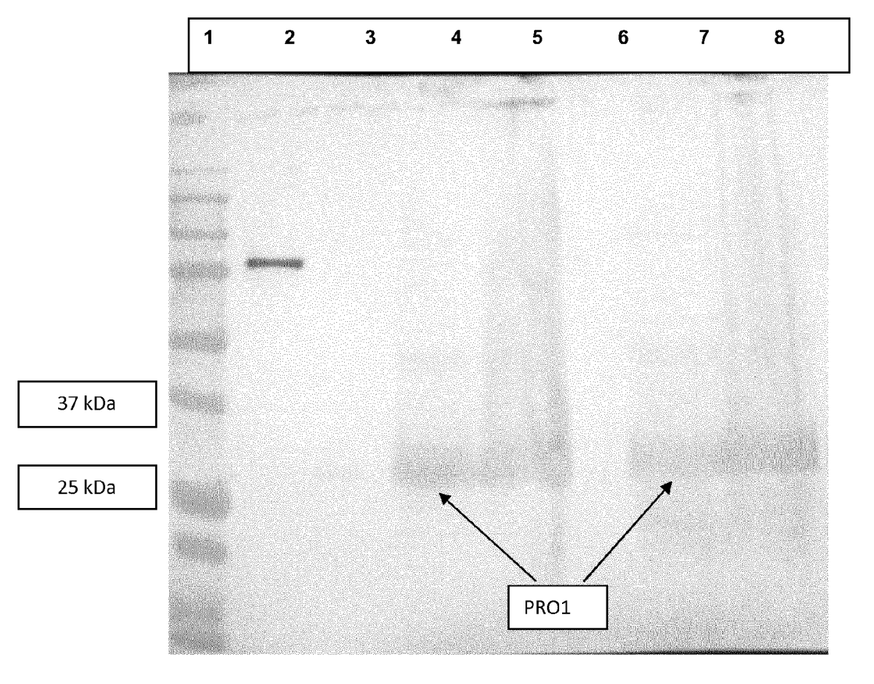
FIG. 1: Detection of BaculoPRO1 by Western blot. 1. Biorad All Blue Standards (161-0373) 2. Positive control with Flag tag 3. Sf9 cells (negative control) 4. Production run #1 (PRO1) soluble fraction (after sonication) 5. Production run #1 (PRO1) cell extract-precipitate 6. empty well 7. Production run #2 (PRO1) soluble fraction (after sonication) 8. Production run #2 (PRO1) cell extract-precipitate.

At the N terminal of the Baculo PRO1 protein, a FLAG tag (Asp-Tyr-Lys-Asp-Asp-Asp-Lys) serves for further identification purposes. The proteins were run in reductive environment and were transferred to a membrane. Monoclonal anti-Flag M2 (Sigma) primary antibody was used in 1:1000 dilution. Anti-mouse IgG Ap (in 1:2500 dilution) was applied as secondary antibody. NBT-BCIP was used for the detection. FIG. 1 shows the results of two production runs.

D. PRO1 Protein is Immunoreactive with Anti-PCV2 Antibodies

A sandwich-type ELISA as disclosed below was used to determine the immunogenic specificity of PRO1.

Coating: monoclonal antibody specific for PCV2 (36F1 from Ingenasa) is allowed to adsorb to the surface of the plastic microplate (ELISA plate). After an incubation period the coating solution is removed and the plate is washed.

The antigen (e.g. BaculoPRO1) is added to the test. After incubation, the unbound antigen is removed and the plate is washed.

Conjugate/secondary antibody: monoclonal antibody specific for PCV2 labeled with biotin (conjugate) is added to the test plate. After incubation, the unbound biotin-linked antibodies are removed and the plate is washed.

A solution of tetrametil-benzidine and hydrogen peroxide mixture (substrate) is added to each well to visualize the bound anti-PCV2 conjugate by a colour reaction catalyzed by the enzyme. The reaction is stopped by sulphuric acid.

The absorbance is read at 450 nm in a spectrophotometer (ELISA reader). The intensity of the signal is proportional to the quantity of antigen present in the sample. The net sample concentrations are calculated on the base of the dilution factors with an ELISA evaluation program.

The results show that PRO1 is immunoreactive with an anti-PCV2 antibody.

E. PRO1 Induces a Protective Immune Response In Vivo

The safety, immunogenicity and efficacy of PRO1 protein as a vaccine were evaluated in 3-week-old pigs with maternal antibody against PCV2.

Three-week-old piglets were selected from a PCV2 sero-positive, conventional sow farm. Selected animals were transported to the experimental facilities and were acclimatized for 5 days until the first vaccination. During this period animals were weighed and blood samples were taken to assess the serological status of the piglets using an indirect immunfluorescence (IIF) assay (see below). Piglets were then divided into four groups, each containing 7 animals.

On day 0, one group of the piglets was vaccinated with 10 µg of BaculoPRO1 subunit vaccine (with adjuvant). Another group was vaccinated with 20 µg of a reference vaccine (Porcilis PCV$^R$) and two control groups (a challenged group and a non-challenged control) were also involved in the trial. Two ml volume of the vaccines (or PBS) was injected by intramuscular route. On day 21, three weeks after vaccination, all the pigs (except the negative controls) were challenged by intranasal administration of PCV2B Rm virus suspension containing 5 log 10 TCID50/ml of the strain (3 ml/nostril, 6 ml/piglet). Rectal temperatures were recorded 3 days before the first vaccination (days −3, −2, −1, on day 0 before vaccination and 4 hours after vaccination and on days 1, 2 and 3).

Blood samples were taken 5 days before the first vaccination (day −5), 10 days after vaccination (day 10), at challenge (day 21) and on days 37 and 44 for quantitative PCR. On day 44 (23 days after challenge) all pigs were euthanized and subjected to necropsy. Tonsils, lymph nodes were collected for quantitative PCR and immunohistochemistry.

Clinical Symptoms:

No clinical signs attributable to the vaccines or to the challenge virus were observed during the experiment.

Real time PCR was performed according to the method described by Brunborg et al. (2004, Quantitation of porcine circovirus type 2 isolated from serum/plasma and tissue samples of healthy pigs and pigs with postweaning multi-systemic wasting syndrome using a TaqMan-based real-time PCR (Journal of Virological Methods 122: 171-178)). PCV2 viral load was quantified using plasmid DNA containing PCV2 sequences. The PCV2 copy numbers of the lymph nodes and the number of viraemic animals are shown in the table below.

| Groups | Group geo mean PCV2 copy number/ml in Mesenterial LN | Number of viraemic pigs/total number of pigs on D44 |
|---|---|---|
| A: BaculoPRO1 + adjuvant | 3.08E+04 | 0/7 |
| B: Reference vaccine | 3.30E+03 | 0/7 |
| Positive control: PBS + challenge | 1.87E+06 | 4/7 |
| Negative control | — | 0/7 |

NO viraemic pigs were found in Group A. Furthermore, the PCV2 copy numbers were substantially reduced in Group A as compared to positive control. The difference between Group A and B was not significant. In the positive control group, the PCV2 copy numbers of the lymph nodes were significantly high and 4 viraemic animals were found.

Immunohistochemistry:

Immunohistochemistry was performed based on the method described by Opriessnig et al. (2007; Opriessnig T, Meng X, Halbur P: 2007, Porcine circovirus type 2-associated disease: Update on current terminology, clinical manifestations, pathogenesis, diagnosis, and intervention strategies J Vet Diagn Invest 19: 591-615). 36A9 monoclonal antibody produced in mouse and an EnVision anti-mouse HRP kit (Dako, Glostrup, Denmark) was used for the detection. Samples were scored according to the following criteria:

0=no antigen
1=antigen is detected in less than 10% of the follicles
2=antigen is detected in 10-50% of the follicles
3=antigen is detected in more than 50% of the follicles Viral antigen was detected in the cytoplasm and nucleus of the macrophages.

| Groups | Mediastinal lymph nodes | Mesenterial lymph nodes | Inguinal lymph nodes |
|---|---|---|---|
| A: Baculo PRO1 + adjuvant | 0 | 0 | 0 |
| B: Reference vaccine | 0 | 0 | 0 |
| Positive control | 11 | 2 | 1 |
| Negative control | 0 | 0 | 0 |

No positive samples were found in the vaccinated groups with immunohistochemistry.

The above results show that the BaculoPRO1 vaccinated group was clearly protected against PCV2B challenge. The results show PRO1 is effective in vivo and induces a strong protective immune response against naturally occurring PCV2 virus, even at doses as low as 10 µg. A cellular immune response was also induced by PRO1, as measured by IFNgamma release (data not shown). Furthermore, at half dose (10 µg vs 20 µg), the protection obtained with the vaccine of the invention was similar to that provided by the reference vaccine, showing a very potent effect of the synthetic proteins of the invention.

LIST OF SEQUENCES (PRO1)

SEQ ID NO: 1

ATGGCATCCTTCACCAAAAAAAAATTCAAAAAGAAGAAAAACAAACAAAAACTCATGTCTCACAAGTCGTCAAAAAG

AAGACTAGAGTCTTGCAAACAAAATACAAATTCAAATGGAAAAAGAGAAAGGGAGTCTTGAACACCAGATTGTCTAGA

ACCTTCGGTTACACCATTAAGAGAACCACCGTCAAAACCCCATCTTGGGCTGTCGATATGATGAGATTCAACATCAAC

GATTTCGTCCCACCTGGTGGTGGATCAAACCCTAGATCCGTTCCATTCGAGTACTACAGAATCAGAAAAGTCAAAGTC

LIST OF SEQUENCES

```
GAGTTCTGGCCATGCTCTCCTATTACTCAGGGTGATAGAGGAGTTGGATCAACTGCCGTCATCTTGGATGACAACTTC

GTCACTAAGGCTACTGCCTTGACCTACGATCCTTACGTCAATTACTCTAGTAGACACACCATCACCCAACCATTCTCA

TACCATTCCAGATACTTCACTCCAAAACCTGTCTTGGACTCAACCATCGATTACTTTCAACCAAACAACAAGAGAAAC

CAATTGTGGTTGAGATTGCAAACTGCCGGTAACGTCGATCATGTCGGATTGGGAACCGCCTTCGAAAACTCCAAATAC

GACCAGGAGTACAACATTAGAGTCACCATGTACGTCCAATTCAGAGAGTTCAACTTGAAGGACCCACCATTGAACCCA

TAA
```

(PRO1)

SEQ ID NO: 2
```
MASFTKKKFKKKKNKTKTHVSQVVKKKTRVLQTKYKFKWKKRKGVLNTRLSRTFGYTIKRTTVKTPSWAVDMMRFNIN

DFVPPGGGSNPRSVPFEYYRIRKVKVEFWPCSPITQGDRGVGSTAVILDDNFVTKATALTYDPYVNYSSRHTITQPFS

YHSRYFTPKPVLDSTIDYFQPNNKRNQLWLRLQTAGNVDHVGLGTAFENSKYDQEYNIRVTMYVQFREFNLKDPPLNP
```

(PRO2)

SEQ ID NO: 3
```
ATGGCTTCTTTCACCAAAAAAAAATTCAAAAAAAAAAAAACACAAACCAAAAACCCATGTCGGTCAAGTCTTGAAAAAA

AAGACCTGGGTCTTGCACACTAAACACAAATTCAAATGGAAAAGAGAAACGGAATCTTCAACGCCAGATTGTCTAGA

ACTTTCGGTTACACCATTAAGAGAACCACCGTCAAAACACCATCTTGGGCTGTCGACATGTTGAGATTCAACATCAAC

GATTTCTTGCCACCTGGTGGAGGATCAAACCCTAGATCCGTCCCTTTCGAATACTACAGAATCAGAAAAATCAAAGTC

GAGTTCTGGCCATGCTCACCTGTTACTCAAGGAGACAGAGGAGTTGGATCATCTGCAATCATCTTGGACGACAACTTC

GTTCCAAAAGCAAACGCTTTGACCTACGACCCTTACATCAATTACTCTAGTAGACACACCATCACCCAACCATTCACT

TACCATTCCAGATACTTCACCCCTAGACCTGTCTTGGATTCCACTATCAACTACTTCCAACCAAACAACAAAAAAAAC

CAATTGTGGTTGAGATTGCAAACTGCCGGTAATATCGATCATGTCGGATTGGGAACTGCTTTCGACAATTCCATCTAC

GATCAGGAGTACAACATTAGAATCACCATGTACGTTCAATTCAGAGAGTTTTCATTGAAGGACCCACCTTTGAACCCA

TAA
```

(PRO2)

SEQ ID NO: 4
```
MASFTKKKFKKKKHKPKTHVGQVLKKKTWVLHTKHKFKWKKRNGIFNARLSRTFGYTIKRTTVKTPSWAVDMLRFNIN

DFLPPGGGSNPRSVPFEYYRIRKIKVEFWPCSPVTQGDRGVGSSAIILDDNFVPKANALTYDPYINYSSRHTITQPFT

YHSRYFTPRPVLDSTINYFQPNNKKNQLWLRLQTAGNIDHVGLGTAFDNSIYDQEYNIRITMYVQFREFSLKDPPLNP
```

(PRO3)

SEQ ID NO: 5
```
ATGGCCTCTTTCACCAAAAAAAAATTCAAAAAAAAAAAAACAAACCAAAAACCCATGTCTCACAAGTCTTGAAAAAA

AAGACCTGGGTCTTGCACACTAAACACAAATTCAAATGGAAAAGAGAAACGGAATCTTCAACGCCAGATTGTCTAGA

ACTTTCGGTTACACCATTAAGAGAACCACCGTCAAAACTCCATCTTGGGCTGTCGACATGTTGAGATTCAACATCAAC

GATTTCTTGCCACCTGGTGGAGGATCAAACCCTAGATCCGTCCCTTTCGAATACTACAGAATCAGAAAAATCAAAGTC

GAGTTCTGGCCATGCTCCCCTGTTACTCAAGGAGATAGAGGAGTCGGTTCATCCGCTATCATTTTGGACGACAACTTC

GTTCCAAAGGCCAATGCCTTGACTTACGACCCATACGTCGATTACTCTAGTAGACACACCATCACCCAACCATTCTCA

TACCATTCCAGATACTACACCCCTAAACCTGTCTTGGACTCTTCCATCGACTACTTCCAACCAAACAACAAAAAAAAC

CAATTGTGGTTGAGATTGCAAACTGCCGGTAACGTCGACCATGTCGGATTGGGAATTGCCTTCGAAAACTCCATTTAC

GACCAGGAGTACAACATTAGAATCACCATGTACGTTCAATTCAGAGAGTTCGACTTGAAGGACCCACCTTTGAACCCA

TAA
```

LIST OF SEQUENCES (PRO3)                                                                    SEQ ID NO: 6
MASFTKKKFKKKKNKPKTHVSQVLKKKTWVLHTKHKFKWKKRNGIFNARLSRTFGYTIKRTTVKTPSWAVDMLRFNIN
DFLPPGGGSNPRSVPFEYYRIRKIKVEFWPCSPVTQGDRGVGSSAIILDDNFVPKANALTYDPYVDYSSRHTITQPFS
YHSRYYTPKPVLDSSIDYFQPNNKKNQLWLRLQTAGNVDHVGLGIAFENSIYDQEYNIRITMYVQFREFDLKDPPLNP

SEQ ID NO: 7
SFTKKKFKKK K(NorH) K(TorP) KTHV(SorG)Q V(VorL) KKKT(RorW) VL(QorH) TK(YorH) KFKWKKR

SEQ ID NO: 8: Pig albumin domain 1
MKWVTFISLLFLFSSAYSRGVFRRDTYKSEIAHRFKDLGEQYFKGLVLIAFSQHLQQCPYEEHVKLVREVTEFAKTCV
ADESAENCDKSIHTLFGDKLCAIPSLREHYGDLADCCEKEEPERNECFLQHKNDNPDIPKLKPDPVALCADFQEDEQK
FWGKYLYEIARRHPYFYAPELLYYAITYKDVFSECCQAADKAACLLPKIEHLREKVLTSAAKQRLK SEQ ID NO: 9: Pig albumin
MKWVTFISLLFLFSSAYSRGVFRR DTYKSEIAHRFKDLGEQYFKGLVLIAFSQHLQQCPYEEHVKLVREVTEFAKTCVADESAENCDKSIHTLFGDKLCAIP
SLREHYGDLADCCEKEEPERNECFLQHKNDNPDIPKLKPDPVALCADFQEDEQKFWGKYLYEIARRHPYFYAPELLYY
AIIYKDVFSECCQAADKAACLLPKIEHLREKVLTSAAKQRLK
CASIQKFGERAFKAWSLARLSQRFPKADFTEISKIVTDLAKVHKECCHGDLLECADDRADLAKYICENQDTISTKLKE
CCDKPLLEKSHCIAEAKRDELPADLNPLEHDFVEDKEVCKNYKEAKHVFLGTFLYEYSRRHPDYSVSLLLRIAKIYEA
TLEDCCAKEDPPACYATVFDKFQPLVDEPKNLIKQNCELFEKLGEYGFQNALIVRYTKKVPQVSTPTLVEVARKLGLV
GSRCCKRPEEERLSCAEDYLSLVLNRLCVLHEKTPVSEKVTKCCTESLVNRRPCFSALTPDETYKPKEFVEGTFTFHA
DLCTLPEDEKQIKKQTALVELLKHKPHATEEQLRTVLGNFAAFVQKCCAAPDHEACFAVEGPKFVIEIRGILA SEQ ID NO: 10: Flag
DYKDDDDK

---

The invention claimed is:

1. An isolated protein comprising the amino acid sequence of SEQ ID NO: 2, 4, or 6, or an amino acid sequence having at least 90% identity over the entire length of SEQ ID NO: 2, 4, or 6.

2. The isolated protein of claim 1, further comprising a carrier amino acid sequence.

3. The isolated protein of claim 1, which comprises an amino acid sequence having at least 95% identity to the amino acid sequence of SEQ ID NO: 2, 4, or 6.

4. The isolated protein of claim 1, which comprises SEQ ID NO: 2 or the amino acid sequence having at least 90% identity over the entire length of SEQ ID NO:2.

5. The isolated protein of claim 1, which comprises SEQ ID NO: 2.

6. A composition comprising the isolated protein of claim 1 and, optionally, an excipient and/or an adjuvant.

7. A vaccine composition comprising an immunologically effective amount of the isolated protein of claim 1 and an excipient and/or an adjuvant.

8. An isolated nucleic acid molecule encoding the isolated protein of claim 1.

9. A vector comprising the nucleic acid molecule of claim 8 under the control of a promoter.

10. A composition comprising the nucleic acid of claim 8 and, optionally, an excipient and/or an adjuvant.

11. A composition comprising the vector of claim 9 and, optionally, an excipient and/or an adjuvant.

12. A vaccine composition comprising an immunologically effective amount of the nucleic acid of claim 8 and an excipient and/or an adjuvant.

13. A vaccine composition comprising an immunologically effective amount of the vector of claim 9 and an excipient and/or an adjuvant.

14. A method for treating or preventing a porcine circovirus 2 (PCV2)-associated disease in a non-human mammal, comprising administering to said non-human mammal the isolated protein of claim 1.

15. A method for treating or preventing a PCV2-associated disease in a non-human mammal, comprising administering to said non-human mammal the nucleic acid of claim 8.

16. An isolated transfected cell comprising the nucleic acid of claim 8.

17. A method for producing a protein comprising culturing the cell of claim 16 under conditions allowing expression of the nucleic acid and recovering the protein.

18. A method for treating or preventing a PCV2-associated disease in a non-human mammal, comprising administering to said non-human mammal the vector of claim 9.

19. An isolated transfected cell comprising the vector of claim 9.

* * * * *

SEQUENCE LISTING

<160> NUMBER OF SEQ ID NOS: 10

<210> SEQ ID NO 1
<211> LENGTH: 705
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(705)

<400> SEQUENCE: 1

```
atg gca tcc ttc acc aaa aaa aaa ttc aaa aag aag aaa aac aaa aca        48
Met Ala Ser Phe Thr Lys Lys Lys Phe Lys Lys Lys Lys Asn Lys Thr
1               5                  10                  15 aaa act cat gtc tca caa gtc gtc aaa aag aag act aga gtc ttg caa        96
Lys Thr His Val Ser Gln Val Val Lys Lys Lys Thr Arg Val Leu Gln
            20                  25                  30 aca aaa tac aaa ttc aaa tgg aaa aag aga aag gga gtc ttg aac acc       144
Thr Lys Tyr Lys Phe Lys Trp Lys Lys Arg Lys Gly Val Leu Asn Thr
        35                  40                  45 aga ttg tct aga acc ttc ggt tac acc att aag aga acc acc gtc aaa       192
Arg Leu Ser Arg Thr Phe Gly Tyr Thr Ile Lys Arg Thr Thr Val Lys
    50                  55                  60
```

```
acc cca tct tgg gct gtc gat atg atg aga ttc aac atc aac gat ttc    240
Thr Pro Ser Trp Ala Val Asp Met Met Arg Phe Asn Ile Asn Asp Phe
 65              70                  75                  80 gtc cca cct ggt ggt gga tca aac cct aga tcc gtt cca ttc gag tac    288
Val Pro Pro Gly Gly Gly Ser Asn Pro Arg Ser Val Pro Phe Glu Tyr
                85                  90                  95 tac aga atc aga aaa gtc aaa gtc gag ttc tgg cca tgc tct cct att    336
Tyr Arg Ile Arg Lys Val Lys Val Glu Phe Trp Pro Cys Ser Pro Ile
            100                 105                 110 act cag ggt gat aga gga gtt gga tca act gcc gtc atc ttg gat gac    384
Thr Gln Gly Asp Arg Gly Val Gly Ser Thr Ala Val Ile Leu Asp Asp
        115                 120                 125 aac ttc gtc act aag gct act gcc ttg acc tac gat cct tac gtc aat    432
Asn Phe Val Thr Lys Ala Thr Ala Leu Thr Tyr Asp Pro Tyr Val Asn
    130                 135                 140 tac tct agt aga cac acc atc acc caa cca ttc tca tac cat tcc aga    480
Tyr Ser Ser Arg His Thr Ile Thr Gln Pro Phe Ser Tyr His Ser Arg
145                 150                 155                 160 tac ttc act cca aaa cct gtc ttg gac tca acc atc gat tac ttt caa    528
Tyr Phe Thr Pro Lys Pro Val Leu Asp Ser Thr Ile Asp Tyr Phe Gln
                165                 170                 175 cca aac aac aag aga aac caa ttg tgg ttg aga ttg caa act gcc ggt    576
Pro Asn Asn Lys Arg Asn Gln Leu Trp Leu Arg Leu Gln Thr Ala Gly
            180                 185                 190 aac gtc gat cat gtc gga ttg gga acc gcc ttc gaa aac tcc aaa tac    624
Asn Val Asp His Val Gly Leu Gly Thr Ala Phe Glu Asn Ser Lys Tyr
        195                 200                 205 gac cag gag tac aac att aga gtc acc atg tac gtc caa ttc aga gag    672
Asp Gln Glu Tyr Asn Ile Arg Val Thr Met Tyr Val Gln Phe Arg Glu
    210                 215                 220 ttc aac ttg aag gac cca cca ttg aac cca taa                        705
Phe Asn Leu Lys Asp Pro Pro Leu Asn Pro
225                 230

<210> SEQ ID NO 2
<211> LENGTH: 234
<212> TYPE: PRT
<213> ORGANISM: Artificial sequence
<220> FEATURE:
<223> OTHER INFORMATION: Synthetic Construct

<400> SEQUENCE: 2

Met Ala Ser Phe Thr Lys Lys Phe Lys Lys Lys Asn Lys Thr
 1               5                  10                  15

Lys Thr His Val Ser Gln Val Val Lys Lys Thr Arg Val Leu Gln
                20                  25                  30

Thr Lys Tyr Lys Phe Lys Trp Lys Lys Arg Lys Gly Val Leu Asn Thr
            35                  40                  45

Arg Leu Ser Arg Thr Phe Gly Tyr Thr Ile Lys Arg Thr Val Lys
 50                  55                  60

Thr Pro Ser Trp Ala Val Asp Met Met Arg Phe Asn Ile Asn Asp Phe
 65              70                  75                  80

Val Pro Pro Gly Gly Gly Ser Asn Pro Arg Ser Val Pro Phe Glu Tyr
                85                  90                  95

Tyr Arg Ile Arg Lys Val Lys Val Glu Phe Trp Pro Cys Ser Pro Ile
            100                 105                 110

Thr Gln Gly Asp Arg Gly Val Gly Ser Thr Ala Val Ile Leu Asp Asp
        115                 120                 125

Asn Phe Val Thr Lys Ala Thr Ala Leu Thr Tyr Asp Pro Tyr Val Asn
```

```
                    130                 135                 140
Tyr Ser Ser Arg His Thr Ile Thr Gln Pro Phe Ser Tyr His Ser Arg
145                 150                 155                 160

Tyr Phe Thr Pro Lys Pro Val Leu Asp Ser Thr Ile Asp Tyr Phe Gln
                165                 170                 175

Pro Asn Asn Lys Arg Asn Gln Leu Trp Leu Arg Leu Gln Thr Ala Gly
            180                 185                 190

Asn Val Asp His Val Gly Leu Gly Thr Ala Phe Glu Asn Ser Lys Tyr
        195                 200                 205

Asp Gln Glu Tyr Asn Ile Arg Val Thr Met Tyr Val Gln Phe Arg Glu
    210                 215                 220

Phe Asn Leu Lys Asp Pro Pro Leu Asn Pro
225                 230

<210> SEQ ID NO 3
<211> LENGTH: 705
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(705)

<400> SEQUENCE: 3 atg gct tct ttc acc aaa aaa aaa ttc aaa aaa aaa aaa cac aaa cca        48
Met Ala Ser Phe Thr Lys Lys Lys Phe Lys Lys Lys Lys His Lys Pro
1               5                   10                  15 aaa acc cat gtc ggt caa gtc ttg aaa aaa aag acc tgg gtc ttg cac        96
Lys Thr His Val Gly Gln Val Leu Lys Lys Lys Thr Trp Val Leu His
                20                  25                  30 act aaa cac aaa ttc aaa tgg aaa aag aga aac gga atc ttc aac gcc       144
Thr Lys His Lys Phe Lys Trp Lys Lys Arg Asn Gly Ile Phe Asn Ala
            35                  40                  45 aga ttg tct aga act ttc ggt tac acc att aag aga acc acc gtc aaa       192
Arg Leu Ser Arg Thr Phe Gly Tyr Thr Ile Lys Arg Thr Thr Val Lys
        50                  55                  60 aca cca tct tgg gct gtc gac atg ttg aga ttc aac atc aac gat ttc       240
Thr Pro Ser Trp Ala Val Asp Met Leu Arg Phe Asn Ile Asn Asp Phe
65                  70                  75                  80 ttg cca cct ggt gga gga tca aac cct aga tcc gtc cct ttc gaa tac       288
Leu Pro Pro Gly Gly Gly Ser Asn Pro Arg Ser Val Pro Phe Glu Tyr
                85                  90                  95 tac aga atc aga aaa atc aaa gtc gag ttc tgg cca tgc tca cct gtt       336
Tyr Arg Ile Arg Lys Ile Lys Val Glu Phe Trp Pro Cys Ser Pro Val
                100                 105                 110 act caa gga gac aga gga gtt gga tca tct gca atc atc ttg gac gac       384
Thr Gln Gly Asp Arg Gly Val Gly Ser Ser Ala Ile Ile Leu Asp Asp
            115                 120                 125 aac ttc gtt cca aaa gca aac gct ttg acc tac gac cct tac atc aat       432
Asn Phe Val Pro Lys Ala Asn Ala Leu Thr Tyr Asp Pro Tyr Ile Asn
        130                 135                 140 tac tct agt aga cac acc atc acc caa cca ttc act tac cat tcc aga       480
Tyr Ser Ser Arg His Thr Ile Thr Gln Pro Phe Thr Tyr His Ser Arg
145                 150                 155                 160 tac ttc acc cct aga cct gtc ttg gat tcc act atc aac tac ttc caa       528
Tyr Phe Thr Pro Arg Pro Val Leu Asp Ser Thr Ile Asn Tyr Phe Gln
                165                 170                 175 cca aac aac aaa aaa aac caa ttg tgg ttg aga ttg caa act gcc ggt       576
Pro Asn Asn Lys Lys Asn Gln Leu Trp Leu Arg Leu Gln Thr Ala Gly
```

```
                    180                 185                 190
aat atc gat cat gtc gga ttg gga act gct ttc gac aat tcc atc tac    624
Asn Ile Asp His Val Gly Leu Gly Thr Ala Phe Asp Asn Ser Ile Tyr
            195                 200                 205 gat cag gag tac aac att aga atc acc atg tac gtt caa ttc aga gag    672
Asp Gln Glu Tyr Asn Ile Arg Ile Thr Met Tyr Val Gln Phe Arg Glu
210                 215                 220 ttt tca ttg aag gac cca cct ttg aac cca taa                        705
Phe Ser Leu Lys Asp Pro Pro Leu Asn Pro
225                 230

<210> SEQ ID NO 4
<211> LENGTH: 234
<212> TYPE: PRT
<213> ORGANISM: Artificial sequence
<220> FEATURE:
<223> OTHER INFORMATION: Synthetic Construct

<400> SEQUENCE: 4

Met Ala Ser Phe Thr Lys Lys Phe Lys Lys Lys His Lys Pro
1               5                   10                  15

Lys Thr His Val Gly Gln Val Leu Lys Lys Lys Thr Trp Val Leu His
            20                  25                  30

Thr Lys His Lys Phe Lys Trp Lys Lys Arg Asn Gly Ile Phe Asn Ala
        35                  40                  45

Arg Leu Ser Arg Thr Phe Gly Tyr Thr Ile Lys Arg Thr Thr Val Lys
    50                  55                  60

Thr Pro Ser Trp Ala Val Asp Met Leu Arg Phe Asn Ile Asn Asp Phe
65                  70                  75                  80

Leu Pro Pro Gly Gly Gly Ser Asn Pro Arg Ser Val Pro Phe Glu Tyr
                85                  90                  95

Tyr Arg Ile Arg Lys Ile Lys Val Glu Phe Trp Pro Cys Ser Pro Val
            100                 105                 110

Thr Gln Gly Asp Arg Gly Val Gly Ser Ser Ala Ile Ile Leu Asp Asp
        115                 120                 125

Asn Phe Val Pro Lys Ala Asn Ala Leu Thr Tyr Asp Pro Tyr Ile Asn
    130                 135                 140

Tyr Ser Ser Arg His Thr Ile Thr Gln Pro Phe Thr Tyr His Ser Arg
145                 150                 155                 160

Tyr Phe Thr Pro Arg Pro Val Leu Asp Ser Thr Ile Asn Tyr Phe Gln
                165                 170                 175

Pro Asn Asn Lys Lys Asn Gln Leu Trp Leu Arg Leu Gln Thr Ala Gly
            180                 185                 190

Asn Ile Asp His Val Gly Leu Gly Thr Ala Phe Asp Asn Ser Ile Tyr
        195                 200                 205

Asp Gln Glu Tyr Asn Ile Arg Ile Thr Met Tyr Val Gln Phe Arg Glu
    210                 215                 220

Phe Ser Leu Lys Asp Pro Pro Leu Asn Pro
225                 230

<210> SEQ ID NO 5
<211> LENGTH: 705
<212> TYPE: DNA
<213> ORGANISM: Artificial sequence
<220> FEATURE:
<223> OTHER INFORMATION: Synthetic polynucleotide
<220> FEATURE:
<221> NAME/KEY: CDS
<222> LOCATION: (1)..(705)
```

<400> SEQUENCE: 5

```
atg gcc tct ttc acc aaa aaa aaa ttc aaa aaa aaa aaa aac aaa cca      48
Met Ala Ser Phe Thr Lys Lys Lys Phe Lys Lys Lys Lys Asn Lys Pro
1               5                   10                  15 aaa acc cat gtc tca caa gtc ttg aaa aaa aag acc tgg gtc ttg cac      96
Lys Thr His Val Ser Gln Val Leu Lys Lys Lys Thr Trp Val Leu His
            20                  25                  30 act aaa cac aaa ttc aaa tgg aaa aag aga aac gga atc ttc aac gcc     144
Thr Lys His Lys Phe Lys Trp Lys Lys Arg Asn Gly Ile Phe Asn Ala
        35                  40                  45 aga ttg tct aga act ttc ggt tac acc att aag aga acc acc gtc aaa     192
Arg Leu Ser Arg Thr Phe Gly Tyr Thr Ile Lys Arg Thr Thr Val Lys
50                  55                  60 act cca tct tgg gct gtc gac atg ttg aga ttc aac atc aac gat ttc     240
Thr Pro Ser Trp Ala Val Asp Met Leu Arg Phe Asn Ile Asn Asp Phe
65                  70                  75                  80 ttg cca cct ggt gga gga tca aac cct aga tcc gtc cct ttc gaa tac     288
Leu Pro Pro Gly Gly Gly Ser Asn Pro Arg Ser Val Pro Phe Glu Tyr
                85                  90                  95 tac aga atc aga aaa atc aaa gtc gag ttc tgg cca tgc tcc cct gtt     336
Tyr Arg Ile Arg Lys Ile Lys Val Glu Phe Trp Pro Cys Ser Pro Val
            100                 105                 110 act caa gga gat aga gga gtc ggt tca tcc gct atc att ttg gac gac     384
Thr Gln Gly Asp Arg Gly Val Gly Ser Ser Ala Ile Ile Leu Asp Asp
        115                 120                 125 aac ttc gtt cca aag gcc aat gcc ttg act tac gac cca tac gtc gat     432
Asn Phe Val Pro Lys Ala Asn Ala Leu Thr Tyr Asp Pro Tyr Val Asp
130                 135                 140 tac tct agt aga cac acc atc acc caa cca ttc tca tac cat tcc aga     480
Tyr Ser Ser Arg His Thr Ile Thr Gln Pro Phe Ser Tyr His Ser Arg
145                 150                 155                 160 tac tac acc cct aaa cct gtc ttg gac tct tcc atc gac tac ttc caa     528
Tyr Tyr Thr Pro Lys Pro Val Leu Asp Ser Ser Ile Asp Tyr Phe Gln
                165                 170                 175 cca aac aac aaa aaa aac caa ttg tgg ttg aga ttg caa act gcc ggt     576
Pro Asn Asn Lys Lys Asn Gln Leu Trp Leu Arg Leu Gln Thr Ala Gly
            180                 185                 190 aac gtc gac cat gtc gga ttg gga att gcc ttc gaa aac tcc att tac     624
Asn Val Asp His Val Gly Leu Gly Ile Ala Phe Glu Asn Ser Ile Tyr
        195                 200                 205 gac cag gag tac aac att aga atc acc atg tac gtt caa ttc aga gag     672
Asp Gln Glu Tyr Asn Ile Arg Ile Thr Met Tyr Val Gln Phe Arg Glu
210                 215                 220 ttc gac ttg aag gac cca cct ttg aac cca taa                         705
Phe Asp Leu Lys Asp Pro Pro Leu Asn Pro
225                 230
```

<210> SEQ ID NO 6
<211> LENGTH: 234
<212> TYPE: PRT
<213> ORGANISM: Artificial sequence
<220> FEATURE:
<223> OTHER INFORMATION: Synthetic Construct

<400> SEQUENCE: 6

```
Met Ala Ser Phe Thr Lys Lys Lys Phe Lys Lys Lys Lys Asn Lys Pro
1               5                   10                  15

Lys Thr His Val Ser Gln Val Leu Lys Lys Lys Thr Trp Val Leu His
            20                  25                  30
```

```
Thr Lys His Lys Phe Lys Trp Lys Arg Asn Gly Ile Phe Asn Ala
         35                  40                  45

Arg Leu Ser Arg Thr Phe Gly Tyr Thr Ile Lys Arg Thr Thr Val Lys
 50                  55                  60

Thr Pro Ser Trp Ala Val Asp Met Leu Arg Phe Asn Ile Asn Asp Phe
 65                  70                  75                  80

Leu Pro Pro Gly Gly Gly Ser Asn Pro Arg Ser Val Pro Phe Glu Tyr
                 85                  90                  95

Tyr Arg Ile Arg Lys Ile Lys Val Glu Phe Trp Pro Cys Ser Pro Val
                100                 105                 110

Thr Gln Gly Asp Arg Gly Val Gly Ser Ser Ala Ile Ile Leu Asp Asp
                115                 120                 125

Asn Phe Val Pro Lys Ala Asn Ala Leu Thr Tyr Asp Pro Tyr Val Asp
        130                 135                 140

Tyr Ser Ser Arg His Thr Ile Thr Gln Pro Phe Ser Tyr His Ser Arg
145                 150                 155                 160

Tyr Tyr Thr Pro Lys Pro Val Leu Asp Ser Ser Ile Asp Tyr Phe Gln
                165                 170                 175

Pro Asn Asn Lys Lys Asn Gln Leu Trp Leu Arg Leu Gln Thr Ala Gly
                180                 185                 190

Asn Val Asp His Val Gly Leu Gly Ile Ala Phe Glu Asn Ser Ile Tyr
                195                 200                 205

Asp Gln Glu Tyr Asn Ile Arg Ile Thr Met Tyr Val Gln Phe Arg Glu
        210                 215                 220

Phe Asp Leu Lys Asp Pro Pro Leu Asn Pro
225                 230

<210> SEQ ID NO 7
<211> LENGTH: 40
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (12)..(12)
<223> OTHER INFORMATION: N or H
<220> FEATURE:
<221> NAME/KEY: MISC_FEATURE
<222> LOCATION: (14)..(14)
<223> OTHER INFORMATION: T or P
<220> FEATURE:
<221> NAME/KEY: MISC_FEATURE
<222> LOCATION: (19)..(19)
<223> OTHER INFORMATION: S or G
<220> FEATURE:
<221> NAME/KEY: MISC_FEATURE
<222> LOCATION: (22)..(22)
<223> OTHER INFORMATION: V or L
<220> FEATURE:
<221> NAME/KEY: MISC_FEATURE
<222> LOCATION: (27)..(27)
<223> OTHER INFORMATION: R or W
<220> FEATURE:
<221> NAME/KEY: MISC_FEATURE
<222> LOCATION: (30)..(30)
<223> OTHER INFORMATION: Q or H
<220> FEATURE:
<221> NAME/KEY: MISC_FEATURE
<222> LOCATION: (33)..(33)
<223> OTHER INFORMATION: Y or H

<400> SEQUENCE: 7

Ser Phe Thr Lys Lys Lys Phe Lys Lys Lys Xaa Lys Xaa Lys Thr
 1               5                  10                  15
```

```
His Val Xaa Gln Val Xaa Lys Lys Thr Xaa Val Leu Xaa Thr Lys
        20              25                  30

Xaa Lys Phe Lys Trp Lys Lys Arg
        35              40

<210> SEQ ID NO 8
<211> LENGTH: 222
<212> TYPE: PRT
<213> ORGANISM: Artificial sequence
<220> FEATURE:
<223> OTHER INFORMATION: pig albumin domain 1

<400> SEQUENCE: 8

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys
    210                 215                 220

<210> SEQ ID NO 9
<211> LENGTH: 607
<212> TYPE: PRT
<213> ORGANISM: Sus scrofa

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60
```

-continued

Lys Leu Val Arg Glu Val Thr Glu Phe Ala Lys Thr Cys Val Ala Asp
65                  70                  75                  80

Glu Ser Ala Glu Asn Cys Asp Lys Ser Ile His Thr Leu Phe Gly Asp
                85                  90                  95

Lys Leu Cys Ala Ile Pro Ser Leu Arg Glu His Tyr Gly Asp Leu Ala
            100                 105                 110

Asp Cys Cys Glu Lys Glu Pro Glu Arg Asn Glu Cys Phe Leu Gln
        115                 120                 125

His Lys Asn Asp Asn Pro Asp Ile Pro Lys Leu Lys Pro Asp Pro Val
    130                 135                 140

Ala Leu Cys Ala Asp Phe Gln Glu Asp Glu Gln Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Ile Ile Tyr Lys Asp Val Phe Ser Glu Cys Cys
            180                 185                 190

Gln Ala Ala Asp Lys Ala Ala Cys Leu Leu Pro Lys Ile Glu His Leu
        195                 200                 205

Arg Glu Lys Val Leu Thr Ser Ala Ala Lys Gln Arg Leu Lys Cys Ala
    210                 215                 220

Ser Ile Gln Lys Phe Gly Glu Arg Ala Phe Lys Ala Trp Ser Leu Ala
225                 230                 235                 240

Arg Leu Ser Gln Arg Phe Pro Lys Ala Asp Phe Thr Glu Ile Ser Lys
                245                 250                 255

Ile Val Thr Asp Leu Ala Lys Val His Lys Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Thr Ile Ser Thr Lys Leu Lys Glu Cys Cys Asp Lys
    290                 295                 300

Pro Leu Leu Glu Lys Ser His Cys Ile Ala Glu Ala Lys Arg Asp Glu
305                 310                 315                 320

Leu Pro Ala Asp Leu Asn Pro Leu Glu His Asp Phe Val Glu Asp Lys
                325                 330                 335

Glu Val Cys Lys Asn Tyr Lys Glu Ala Lys His Val Phe Leu Gly Thr
            340                 345                 350

Phe Leu Tyr Glu Tyr Ser Arg Arg His Pro Asp Tyr Ser Val Ser Leu
        355                 360                 365

Leu Leu Arg Ile Ala Lys Ile Tyr Glu Ala Thr Leu Glu Asp Cys Cys
    370                 375                 380

Ala Lys Glu Asp Pro Pro Ala Cys Tyr Ala Thr Val Phe Asp Lys Phe
385                 390                 395                 400

Gln Pro Leu Val Asp Glu Pro Lys Asn Leu Ile Lys Gln Asn Cys Glu
                405                 410                 415

Leu Phe Glu Lys Leu Gly Glu Tyr Gly Phe Gln Asn Ala Leu Ile Val
            420                 425                 430

Arg Tyr Thr Lys Lys Val Pro Gln Val Ser Thr Pro Thr Leu Val Glu
        435                 440                 445

Val Ala Arg Lys Leu Gly Leu Val Gly Ser Arg Cys Cys Lys Arg Pro
    450                 455                 460

Glu Glu Glu Arg Leu Ser Cys Ala Glu Asp Tyr Leu Ser Leu Val Leu
465                 470                 475                 480

Asn Arg Leu Cys Val Leu His Glu Lys Thr Pro Val Ser Glu Lys Val

```
                        485                 490                 495
Thr Lys Cys Cys Thr Glu Ser Leu Val Asn Arg Arg Pro Cys Phe Ser
                500                 505                 510

Ala Leu Thr Pro Asp Glu Thr Tyr Lys Pro Lys Glu Phe Val Glu Gly
            515                 520                 525

Thr Phe Thr Phe His Ala Asp Leu Cys Thr Leu Pro Glu Asp Glu Lys
        530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
                580                 585                 590

Val Glu Gly Pro Lys Phe Val Ile Glu Ile Arg Gly Ile Leu Ala
                595                 600                 605

<210> SEQ ID NO 10
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 10

Asp Tyr Lys Asp Asp Asp Asp Lys
1               5
```